(12) United States Patent
Chiang et al.

(10) Patent No.: US 11,786,217 B2
(45) Date of Patent: Oct. 17, 2023

(54) INTRA-NEEDLE ULTRASOUND SYSTEM AND ITS METHOD OF USE FOR ANALYSIS, TRACKING, AND DISPLAY OF PLEURA IN MILLIMETER SCALE RESOLUTION

(71) Applicants: National Yang Ming Chiao Tung University, Taipei (TW); Taipei Veterans General Hospital, Taipei (TW)

(72) Inventors: Huihua Chiang, Taipei (TW); Chien-Kun Ting, Taipei (TW); Shu-Wei Liao, Taipei (TW); Fu-Wei Su, Taipei (TW); Ching-Fang Yang, Taipei (TW); Chia-Wei Yang, Taipei (TW)

(73) Assignees: NATIONAL YANG MING CHIAO TUNG UNIVERSITY, Taipei (TW); TAIPEI VETERANS GENERAL HOSPITAL, Taipei (TW)

( * ) Notice: Subject to any disclaimer, the term of this patent is extended or adjusted under 35 U.S.C. 154(b) by 86 days.

(21) Appl. No.: 16/699,277

(22) Filed: Nov. 29, 2019

(65) Prior Publication Data
US 2020/0214678 A1 Jul. 9, 2020

(30) Foreign Application Priority Data
Jan. 3, 2019 (TW) ................................. 108100218

(51) Int. Cl.
*A61B 8/00* (2006.01)
*A61B 8/08* (2006.01)
(Continued)

(52) U.S. Cl.
CPC .......... *A61B 8/5207* (2013.01); *A61B 8/0841* (2013.01); *A61B 8/4483* (2013.01);
(Continued)

(58) Field of Classification Search
CPC ... A61B 8/5207; A61B 8/0841; A61B 8/4483; A61B 8/461; A61B 8/54; A61B 17/3403;
(Continued)

(56) References Cited

U.S. PATENT DOCUMENTS 5,490,522 A * 2/1996 Dardel ................ A61B 8/0833
600/461
9,087,397 B2 * 7/2015 Hwang .................. G06T 19/00
(Continued)

FOREIGN PATENT DOCUMENTS

CN 103876841 A * 6/2014
CN 203619634 U * 6/2014
(Continued)

*Primary Examiner* — Keith M Raymond
*Assistant Examiner* — Adam D. Kolkin
(74) *Attorney, Agent, or Firm* — Muncy, Geissler, Olds & Lowe, P.C.

(57) ABSTRACT

The invention provides an intra-needle ultrasound system and its method of use for analysis, tracking, and display of pleura in millimeter-scale resolution. This method includes the following steps: Assembling the puncture needle and intra-needle ultrasound transducer, which can generate and receive ultrasound waves at the needle tip. To transform the axial ultrasonic signal into a figure, that can help to identify different anatomic structures according to the corresponding feature of ultrasonic RF (Radio Frequency) signal, and to set the region of interest according to corresponding RF feature of amplitude and depth. This invention can indicate the distance between the ultrasound needle tip and pleura in a real-time fashion, and to identify the best position for anesthetic injection in the paravertebral block (PVB) and the intercostals nerve block (ICNB). The system can also help to avoid damage to the pleura and lung during the nerve block procedure.

2 Claims, 8 Drawing Sheets

(51) Int. Cl.
*A61B 17/34* (2006.01)
*G06T 7/00* (2017.01)

(52) U.S. Cl.
CPC ............... *A61B 8/461* (2013.01); *A61B 8/54* (2013.01); *A61B 17/3403* (2013.01); *G06T 7/0012* (2013.01); *A61B 2017/3413* (2013.01); *G06T 2207/10132* (2013.01); *G06T 2207/30061* (2013.01)

(58) Field of Classification Search
CPC .......... A61B 2017/3413; G06T 7/0012; G06T 2207/10132; G06T 2207/30061
See application file for complete search history.

(56) References Cited

U.S. PATENT DOCUMENTS

| | | | |
|---|---|---|---|
| 2003/0073908 A1* | 4/2003 | Desai | A61B 18/1477 600/464 |
| 2010/0081931 A1* | 4/2010 | Destrempes | G06T 7/12 382/128 |
| 2016/0317621 A1* | 11/2016 | Bright | A61K 31/19 |
| 2017/0091914 A1* | 3/2017 | Halmann | A61B 8/4245 |
| 2017/0245831 A1* | 8/2017 | Nishigaki | A61B 8/461 |
| 2018/0000455 A1* | 1/2018 | Bercoff | A61B 8/5207 |

FOREIGN PATENT DOCUMENTS

| | | |
|---|---|---|
| CN | 107126229 A | 9/2017 |
| JP | 2009172050 A * | 8/2009 |

* cited by examiner

INTRA-NEEDLE ULTRASOUND SYSTEM AND ITS METHOD OF USE FOR ANALYSIS, TRACKING, AND DISPLAY OF PLEURA IN MILLIMETER SCALE RESOLUTION

CROSS-REFERENCE TO RELATED APPLICATIONS

This Non-provisional application claims priority under 35 U.S.C. § 119(a) on Patent Application No(s). TW 108100218 filed in Taiwan, Republic of China, Jan. 3, 2019, the entire contents of which are hereby incorporated by reference.

FIELD OF THE INVENTION

The invention provides an ultrasound system and its method of use for analysis, tracking, and display of pleura in millimeter-scale resolution. Particularly, it is used in Paravertebral Block (PVB) and Intercostals Nerve Block (ICNB) to identify the pleura of a signal feature from ultrasound, and detect the distance between the puncture needle tip and the pleura. It can also help to avoid damage to the lung during the nerve block procedure.

BACKGROUND OF INVENTION

In the present, the main technique for peripheral nerve block in the thoracic region is to inject local anesthetics to block nerve roots of thoracic spine or to infiltrate the spaces with nerves, to achieve pain relief.

Over the past ten years, ultrasonic technology is widely used in the area of anesthesiology and has greatly enhanced the effectiveness and success rate of regional anesthetics. Particularly, in the case of the paravertebral block (PVB) and the intercostal nerve block (ICNB), the medical professionals will perform these procedures under the guidance of surface ultrasonic figure. However, even with ultrasound guidance, the above operations are still facing considerable risks such as accidental pleural puncture or pneumothorax.

The present invention combines a puncture needle and an intra-needle ultrasonic transducer to provide an identification of anatomical structures. It provides a real-time ultrasonic signal during puncture and enhances safety by objectively identifying the lung and surrounding tissues.

SUMMARY OF THE INVENTION

The paravertebral block (PVB) and the intercostal nerve block (ICNB) can provide an excellent analgesic effect. However, at present, it has potential risks. With the existence of several important organs in the chest area, it is a challenge to ensure absolute effectiveness and safety. Therefore, the present invention: (1) Using ultrasound needle probe. The needle-shaped ultrasound probe is placed in the inner side of the puncture needle. The ultrasound probe can measure the distance precisely in real-time with the 0.2 mm axial-resolution, and provide warning function. (2) In previous research, the discovery of the flickering pleura signal in respiratory movement in RF-Mode (Radio Frequency mode) has not been reported. (3) Base on the RF signal, setting a region of interest, analyzing and identifying the flickering pleura signal in respiratory movement with de-correlation value, or FFT spectrum or time-frequency spectrum. And then display and track the dynamic distances between the tip of the puncture needle and the pleura in real-time.

The main object of the present invention is to provide a method and system that can identify the axial depth of puncture by analyzing the characteristics of breath movement and the ultrasonic echo signals, particularly echo signals from the pleura, so as to provide assistance for the puncture needle to reach a target depth accurately.

Furthermore, with the use of external ultrasonic depth measurement, the most common implementation of the above-mentioned anesthesia at present is an oblique downward puncture. Referring to FIG. 1A, the puncture needle goes into the intercostal nerve region with an angle between the needle and the skin; referring to FIG. 1B, as in the oblique downward puncture, the external ultrasonic depth measurement is not parallel to the movement direction of the puncture needle, it is difficult to judge and determine the relation between the length of needle thrust and the actual depth, and the needle tip and its distance from the pleura cannot be easily observed. This may increase the risk of the operation. The present invention further discloses another method of needle puncture. See FIG. 1C, the needle is punctured with an orthogonal or nearly perpendicular angle against the skin before going into the region of intercostal nerve. Thus, the depth of needle thrust equals the actual depth.

As such, the present invention provides a combined method for analyzing, identifying, tracking and ranging pleura breath signal in millimeter-scale resolution, which include: (a) obtaining a plurality of echo ultrasonic signals from the axial depth direction of tissue measured by an ultrasound probe at least 20 times per second, wherein, each echo ultrasonic signal includes an ultrasonic amplitude and a time difference between emission and reception of ultrasonic wave; (b) transforming the time differences between emission and reception of ultrasonic wave into a plurality of axial distances, wherein, the axial distances are a plurality of echo distances between various tissue interface and the ultrasound probe; (c) using the axial distances and the ultrasonic amplitudes to produce a distance and signal amplitude figure according to a length unit and an amplitude unit; and (d) based on the distance and signal amplitude figure, setting a region of interest according to a specific amplitude variation feature and a specific depth variation feature, then displaying the dynamic distances between the tip of the puncture needle and the pleura at least 20 times per second.

Furthermore, the present invention provides a combined system for analyzing, identifying, tracking, ranging and displaying of pleura in millimeter-scale resolution, which includes: an ultrasound device, a signal transceiver and a signal analyzing device with a wired or wireless connection to the ultrasound device.

Said ultrasound device has an ultrasound probe and a puncture needle, wherein, said ultrasound probe is placed in the inner side of the puncture needle, emitting, through a signal transceiver, ultrasonic impulse waves at least 20 times per second. (For example: 50 times per second)

Said signal transceiver, to obtain a plurality of echo ultrasonic signals from the axial depth of tissue puncture by the ultrasound probe, wherein, each echo ultrasonic signal includes an ultrasonic amplitude and a time difference between emission and reception of the ultrasonic wave.

Said signal analyzing device includes: a data processor, connected to the signal receiver, to transform the time differences between emission and reception of the ultrasonic wave into a plurality of axial distances. The axial distances are a plurality of echo distances between various tissue interface and the ultrasound probe, then, according to a length unit and an amplitude unit, a distance and signal amplitude figure is produced; and a display, connected to the data processor, to display the distance and signal amplitude figure, and to set a region of interest according to a specific amplitude variation feature and a specific depth variation feature, then to instantly display and track the dynamic distances between the tip of the puncture needle and the pleura in real time.

The term "pleura" as used in the present invention refers to consisting of the visceral pleura and the parietal pleura.

The term "signal" relative position as used in the present invention is the sequence listed below [ultrasonic noise] (303, 504), [puncture needle tip] (301, 501), [ultrasound probe] (401, 601), [innermost intercostal muscle] (502-602) and [pleura] (302, 402, 503, 603), and the pleura signal that is a useful benchmark for measuring to identify the best position for anesthetic injection.

In order to realize the above-mentioned and other objects, one or more embodiments of the present invention are disclosed and illustrated below. Other features and advantages of the present invention are detailed in the embodiments and claims.

DETAILED DESCRIPTION OF THE INVENTION

The embodiments of the present invention are illustrated in FIGS. 2 to 7.

The present invention provides a combined method for analyzing, identifying, tracking, and ranging pleura breath signal in millimeter-scale resolution. See FIG. 2, its steps include: (a) obtaining a plurality of echo ultrasonic signals of the axial depth of tissue puncture by an ultrasound probe at least 20 times per second, wherein, each echo ultrasonic signal includes an ultrasonic amplitude and a time difference between emission and reception of ultrasonic wave S201; (b) transforming the time differences between emission and reception of ultrasonic wave into a plurality of axial distances, wherein, the axial distances are echo distances between various tissue interface and the ultrasound probe S202; (c) using the axial distances and the ultrasonic amplitudes to produce a distance and signal amplitude figure S203 according to a length unit and an amplitude unit; and (d) based on the distance and signal amplitude figure, setting a region of interest according to a specific amplitude variation feature and a specific depth variation feature, then instant displaying and tracking the dynamic distances between the tip of the puncture needle and the pleura in real time S204.

Preferably, the steps of the method to measure the distance of the target object further include: (e) within an operation period, repeating the operational steps (a) to (c), using different axial depths to obtain a plurality of distance and signal amplitude figures; (f) based on the distance and signal amplitude figures, obtaining a distance and signal time-varying figure according to the operation period; and (g) based on the distance and signal time-varying figure, setting a region of interest according to the amplitude variation feature, the depth variation feature and a cyclic variation feature, then displaying the dynamic distances between the tip of the puncture needle and the pleura. Preferably, the cyclic variation feature is a signal amplitude variant or a signal frequency variant. In one embodiment, the cyclic variation feature is related to the breath, and the two variants can be analyzed using de-correlation value or FFT spectrum or time-frequency spectrum.

Figure 1A:
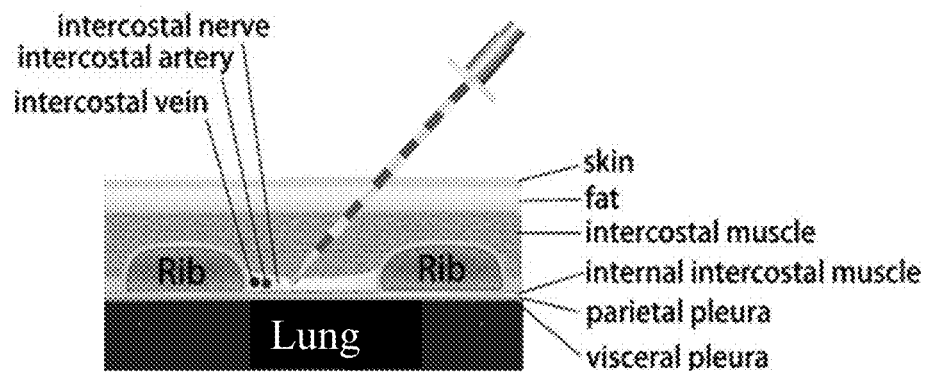
FIG. 1A is an embodiment of oblique downward puncture (in-plane).
Figure 1B:
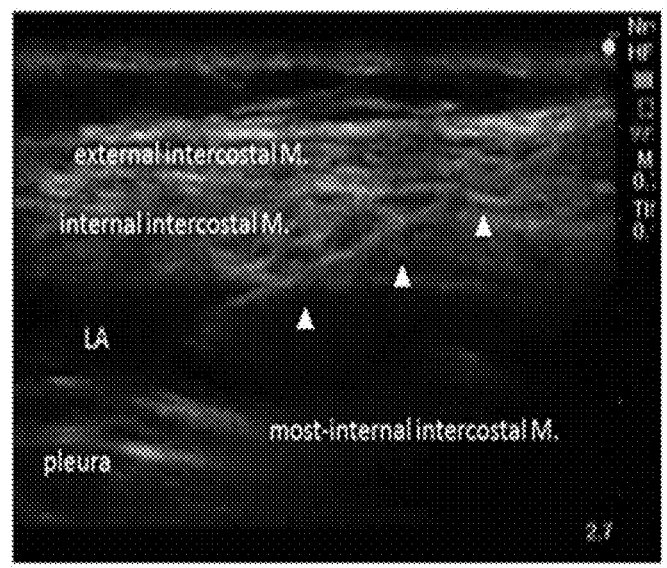
FIG. 1B is an ultrasonic signal diagram of the oblique downward puncture to the schematic diagram.
Figure 1C:
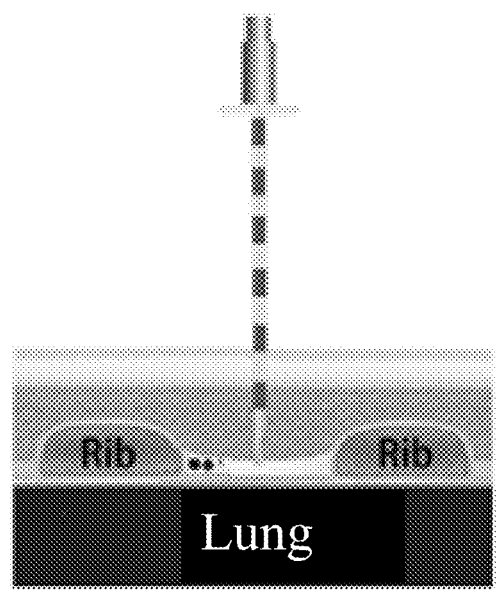
FIG. 1C is an embodiment of orthogonal downward puncture.
Figure 2:
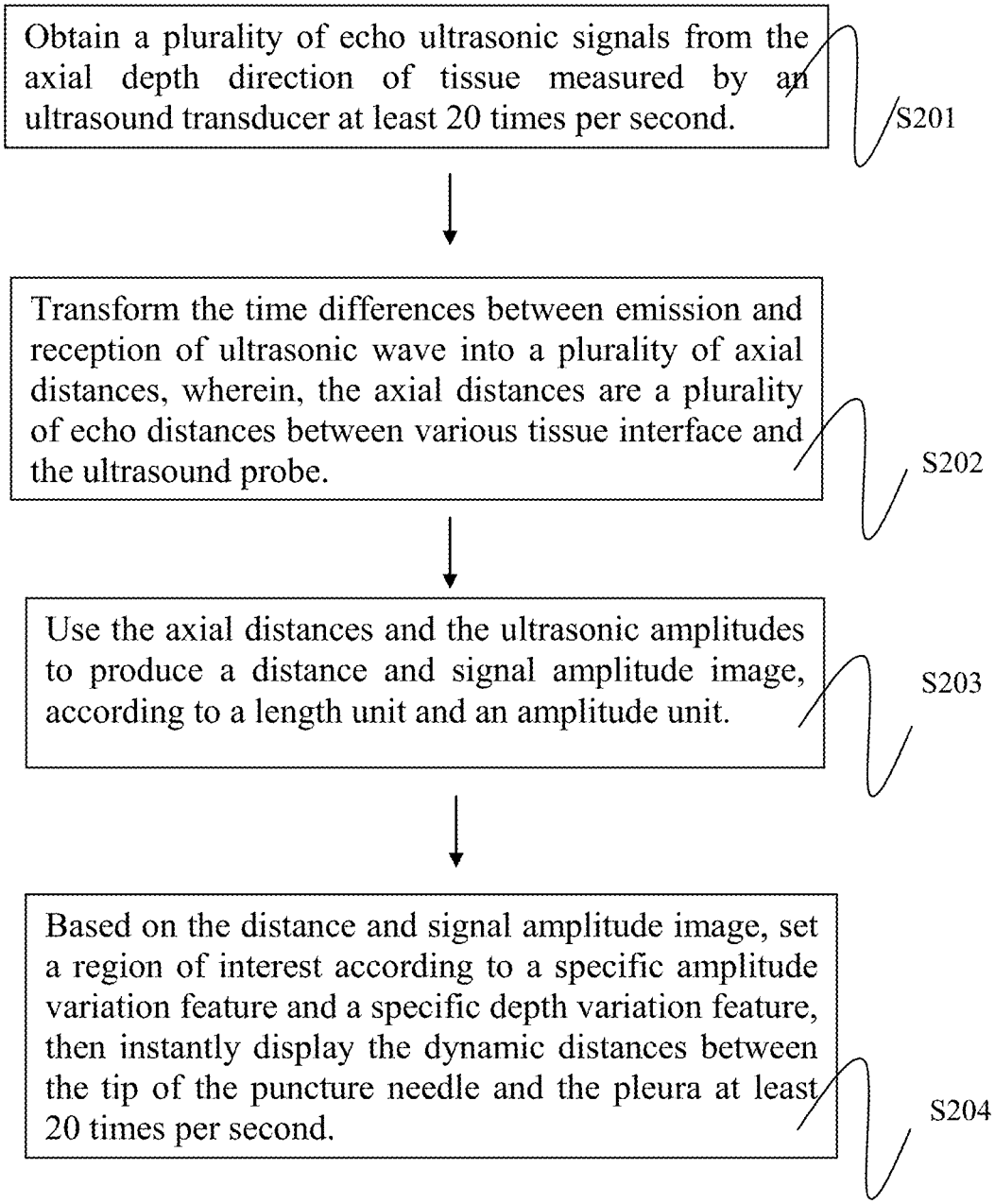
FIG. 2 is a step-by-step process chart of the present invention.
Figure 3:
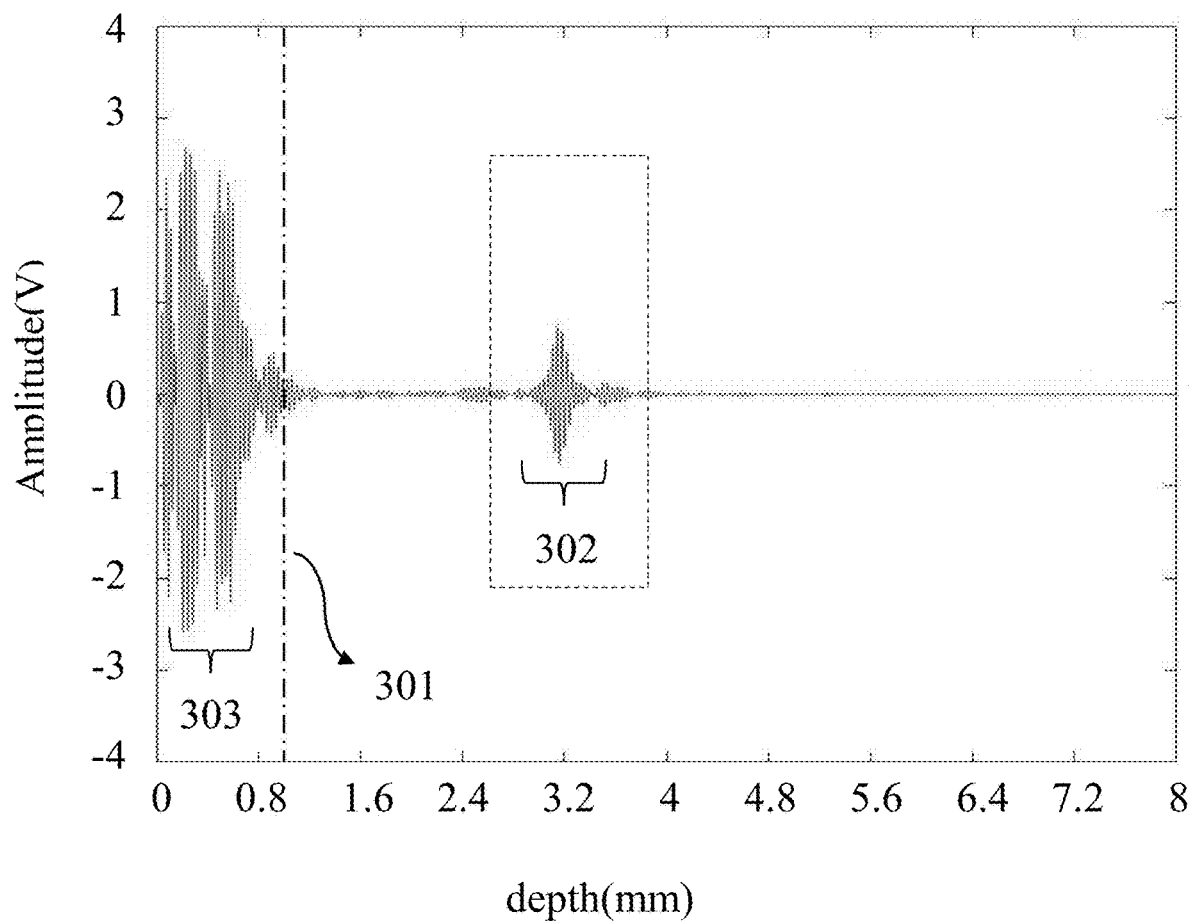
FIG. 3 is a figure showing the distance between the ultrasound probe and the pleura as well as the signal amplitude obtained from PVB by the method of the present invention.
Figure 4:
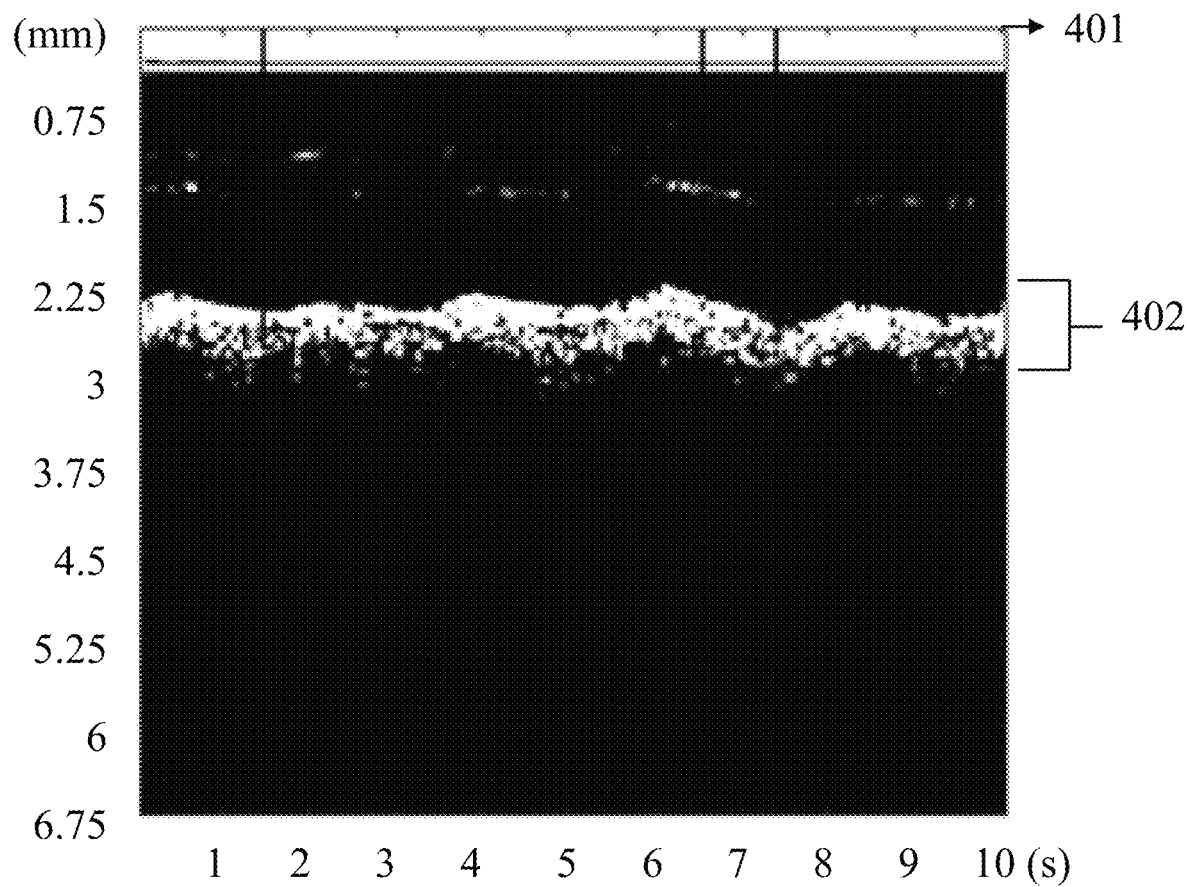
FIG. 4 is a time-varying figure of the distance between the ultrasound probe and the pleura and the signal amplitude obtained from PVB by the method of the present invention (ultrasonic M-mode figure).

In one preferred embodiment, the tissue puncture refers to a region, the paravertebral region, which is formed by the superior costotransverse ligament, pleura, and the transverse processes of the vertebrae. The needle ultrasound probe measures the distance between the tip of the puncture needle and the pleura in real time during the breathing FIG. 3 is a distance and signal amplitude figure obtained from PVB by the ultrasound probe of the present invention. It shows the puncture depths at intervals from the puncture needle tip 301 to the pleura 302; furthermore, referring to FIG. 4, a time-varying figure of the depths and signals obtained from PVB by the ultrasound probe of the present invention, the pleura 402 has cyclic ups and downs along with the breath.

Figure 5:
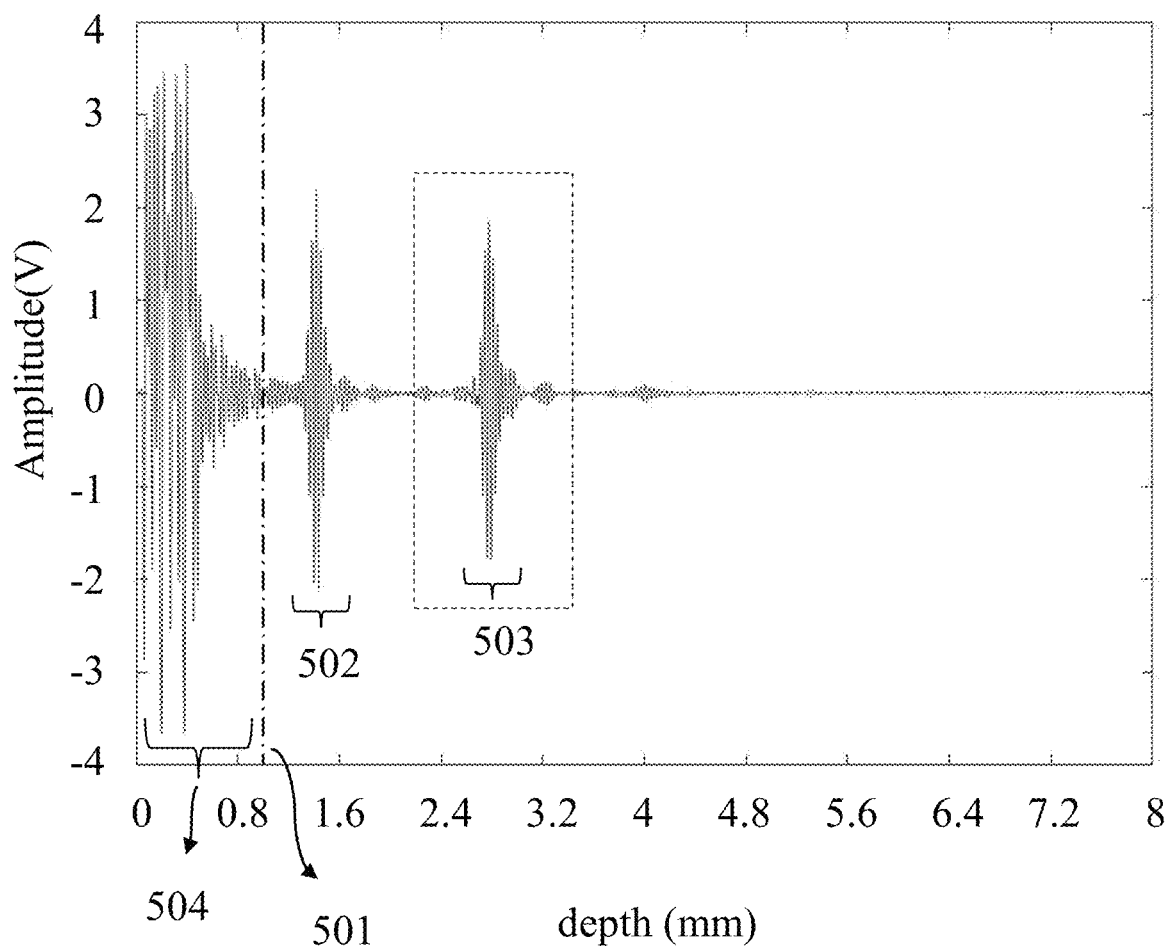
FIG. 5 is a figure showing the distance between the ultrasound probe and the pleura as well as the signal amplitude obtained from ICNB by the method of the present invention.
Figure 6:
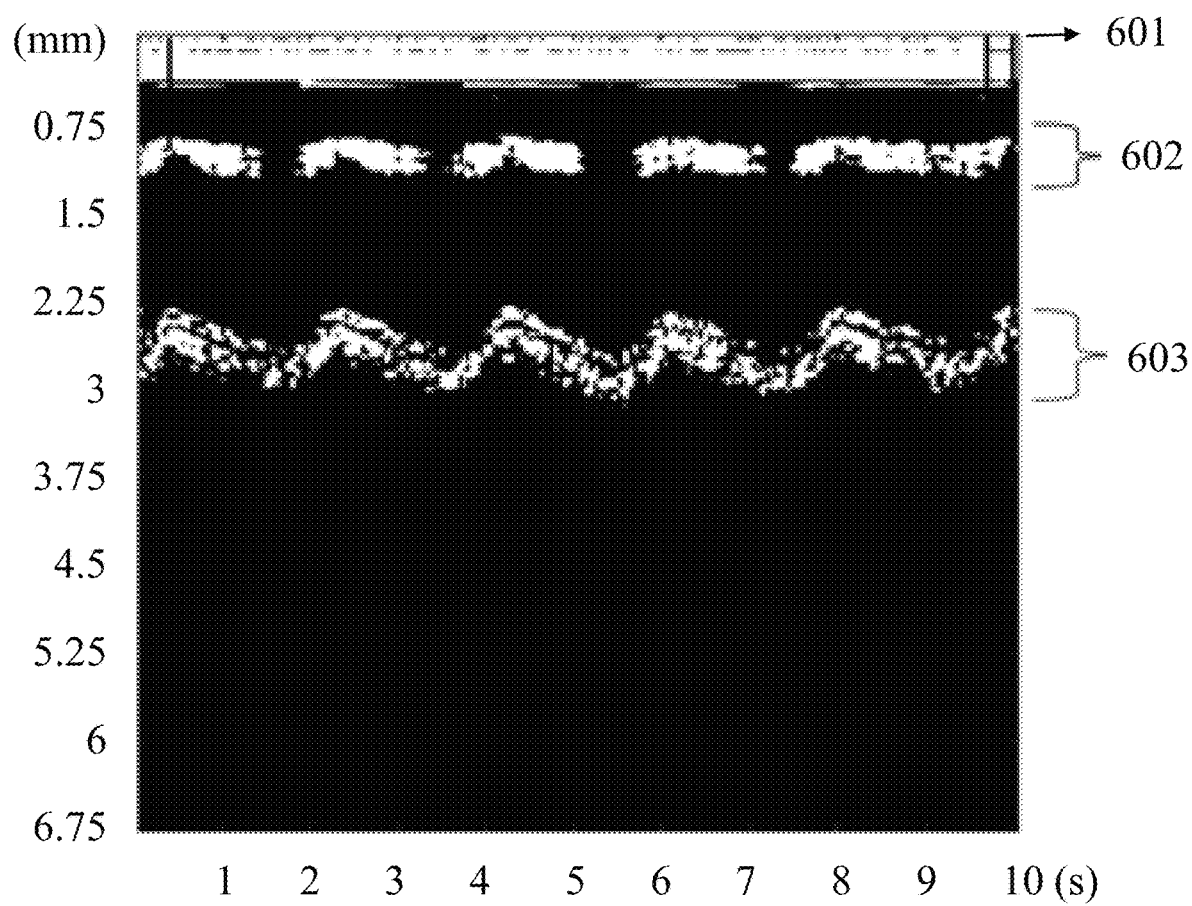
FIG. 6 is a time-varying figure of the distance between the ultrasound probe and the pleura and the signal amplitude obtained from ICNB by the method of the present invention (ultrasonic M-mode figure).

In one preferred embodiment, the tissue puncture refers to a region from an intercostal space to the pleura. The needle ultrasound probe measures the distance among the tip of the puncture needle, the innermost intercostal muscle (IiM) 502 and the pleura in real time during the breathing FIG. 5 is a distance and signal amplitude figure obtained from the intercostal nerve block (ICNB) by the ultrasound probe of the present invention. It shows the puncture depths at intervals from the puncture needle tip 501 to the innermost intercostal muscle (IiM) 502 and the pleura 503; furthermore, referring to FIG. 6, a time-varying figure of the depths and signals obtained from intercostal nerve block (ICNB) by the probe of the present invention, the pleura 603 has cyclic ups and downs along with the breath.

Preferably, the steps of the method further include: when the distance between the pleura and the tip of the puncture needle is closer than a preset distance, a warning signal is produced which is not limited to being expressed in the form of light, sound or symbols.

Figure 7:
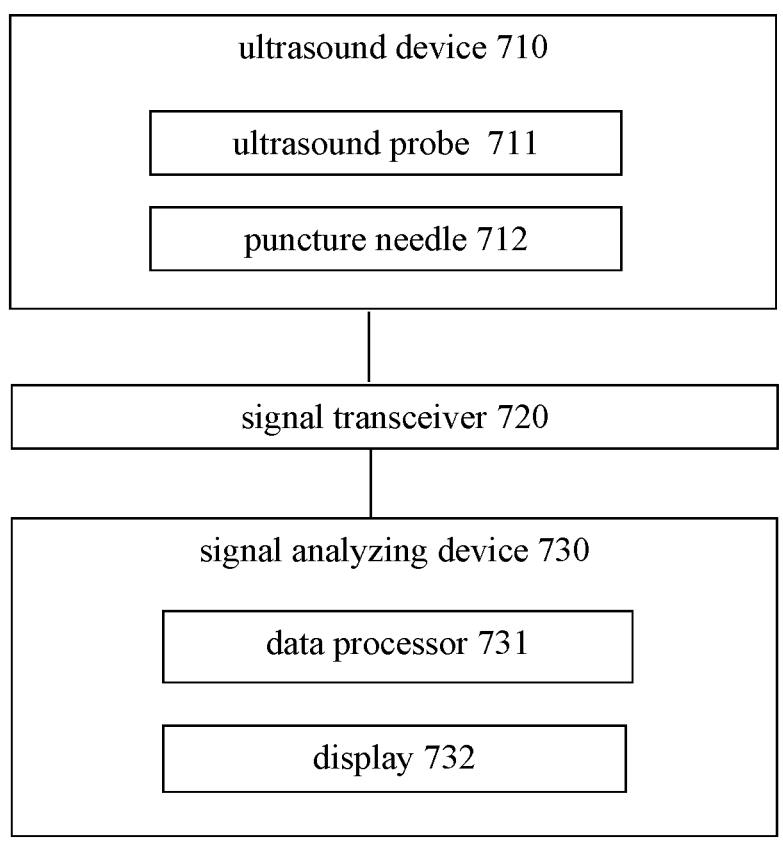
FIG. 7 is a component relationship diagram of the present invention.

The implementation steps of the combined method of the present invention can further be written into a software program. The software program can be saved in record media to be identified and decoded by any micro-processing unit, or in any object or device containing the above record media. With no limit to the form, the above object can be a hard disk, floppy disk, CD-ROM, ZIP, MO, IC chip, RAM, or any object containing the above record media available to those skilled in the art. Referring to FIG. 7, the present invention provides a combined system 700 for analyzing, identifying, tracking, ranging and displaying of pleura in millimeter-scale resolution, which includes: an ultrasound device 710, a signal transceiver 720 and a signal analyzing device 730, with a wired or wireless connection to the signal transceiver 720.

Said ultrasound device 710 has an ultrasound probe 711 and a puncture needle 712, wherein, said ultrasound probe 711 is placed on the inner side from the puncture needle 712, emitting, through a signal transceiver 720, ultrasonic impulse waves at least 20 times per second (For example: 50 times per second). Preferably, the frequency of the ultrasonic impulse wave is 5-40 MHz, and the amplitude is 50-100V.

In one embodiment, the end face of the ultrasound probe 711 is a plane, and the tube end of the puncture needle 712 is a relatively inclined plane; or, the end face of the ultrasound probe 711 and the tube end of the puncture needle 712 are aligned to the same inclined plane, and the same plane is an inclined plane with an included angle of 20 to 50 degrees. Said signal transceiver 720, to obtain a plurality of echo ultrasonic signals of the axial depth of tissue puncture by the ultrasound device 710, wherein, each echo ultrasonic signal includes an ultrasonic amplitude and a time difference between emission and reception of ultrasonic wave.

Said signal analyzing device 730 includes: a signal processor 731, to transform the time differences between emission and reception of the ultrasonic wave into a plurality of axial distances. The axial distances are a plurality of echo distances between various tissue interface and the ultrasound probe, and, according to a length unit and an amplitude unit, a distance and signal amplitude figure is produced; and a display 732, connected to the data processor 731, to display the distance and signal amplitude figure, and to set a region of interest according to a specific amplitude variation feature and a specific depth variation feature, then to instantly display and track the dynamic distances between the tip of the puncture needle 712 and the pleura in real time. Preferably, the data processor 731 to obtain the plurality of distance and signal amplitude figures based on different axial depths, and, based on the distance and signal amplitude figures, to output a distance and signal time-varying figure according to the operation period; and the display 732 displays the distance and signal time-varying figure, and set the region of interest according to the amplitude variation feature, the depth variation feature and a cyclic variation feature, and display the distances between the pleura and the tip of the puncture needle 712.

The features disclosed in the present invention can be realized in any form of combination, and can be substituted by any alternatives with the same, equal or similar objects. Therefore, unless otherwise indicated, each feature disclosed is just an embodiment of one type of an equivalent or similar feature.

The invention claimed is:

1. A combined method for analyzing, identifying, tracking, ranging and displaying pleura breath signal in sub-millimeter-scale resolution, with its steps including:
   (a) obtaining a plurality of echo ultrasonic signals from the axial depth direction of tissue puncture at least 20 times per second by an ultrasound probe, placed in the inner side of a puncture needle and coaxial with the puncture needle, wherein, each echo ultrasonic signal includes an ultrasonic amplitude and a time difference between emission and reception of ultrasonic wave, wherein the ultrasound probe transmits and receives signals coaxially, wherein the tissue puncture refers to a region from an intercostal space to the pleura; the ultrasound probe measures the distance between the tip of the puncture needle and the innermost intercostal muscle (IiM) and between the tip of the puncture needle and the pleura in real time during the breathing;
   (b) transforming the time differences between emission and reception of ultrasonic wave into a plurality of axial distances, the axial distances are a plurality of echo distances between various tissue interface and the ultrasound probe;
   (c) using the axial distances and the ultrasonic amplitudes extracted from radio frequency signals to produce a distance and signal amplitude figure according to a length unit and an amplitude unit;
   (d) based on the distance and signal amplitude figure, setting a region of interest according to a specific amplitude variation feature and a specific depth variation feature, identifying a flickering pleura signal, then instantly displaying and tracking the dynamic distances between a tip of the puncture needle and the pleura;
   (e) within an operation period, repeating the operational steps (a) to (c), using different axial depths to obtain a plurality of distance and signal amplitude figures;
   (f) based on the distance and signal amplitude figures, obtaining a distance and signal time-varying figure according to the operation period; and
   (g) based on the distance and signal time-varying figure, setting a region of interest according to the specific amplitude variation feature, the specific depth variation feature and a cyclic variation feature, then identifying the flickering pleura signal and displaying the dynamic distances between the pleura and the tip of the puncture needle.

2. The method defined in claim 1, wherein its steps further including:
   when the distance between the pleura and the tip of the puncture needle is shorter than a preset distance, a warning signal is produced.

* * * * *